US010169323B2

(12) United States Patent
Clark et al.

(10) Patent No.: US 10,169,323 B2
(45) Date of Patent: *Jan. 1, 2019

(54) DIAGNOSING AUTISM SPECTRUM DISORDER USING NATURAL LANGUAGE PROCESSING

(71) Applicant: International Business Machines Corporation, Armonk, NY (US)

(72) Inventors: Adam T. Clark, Mantorville, MN (US); Brian J. Cragun, Rochester, MN (US); Anthony W. Eichenlaub, Rochester, MN (US); John E. Petri, St. Charles, MN (US); John C. Unterholzner, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 138 days.

This patent is subject to a terminal disclaimer.

(21) Appl. No.: 14/862,815

(22) Filed: Sep. 23, 2015

(65) Prior Publication Data

US 2016/0179786 A1   Jun. 23, 2016

Related U.S. Application Data

(63) Continuation of application No. 14/577,324, filed on Dec. 19, 2014.

(51) Int. Cl.
*A61B 5/16*   (2006.01)
*G06N 7/00*   (2006.01)
(Continued)

(52) U.S. Cl.
CPC .......... *G06F 17/2765* (2013.01); *A61B 5/168* (2013.01); *G06F 17/30663* (2013.01);
(Continued)

(58) Field of Classification Search
CPC .................. G06N 7/005; G06N 99/005; G06F 17/30663; G06F 17/30976; G06F 19/345; A61B 5/168
(Continued)

(56) References Cited

U.S. PATENT DOCUMENTS 7,912,705 B2 * 3/2011 Wasson ................ G06F 17/241
704/9
8,078,465 B2   12/2011 Paul et al.
(Continued)

FOREIGN PATENT DOCUMENTS

WO   2010008568 A1   1/2010
WO   2014062441 A1   4/2014

OTHER PUBLICATIONS

"Analyzing the performance of fuzzy cognitive maps with non-linear hebbian learning algorithm in predicting autistic disorder" Arthi Kannappan, A. Tamilarasi, E.I. Papageorgiou, Expert Systems with Applications, vol. 38, Issue 3, Mar. 2011, pp. 1282-1292.*

(Continued)

*Primary Examiner* — Michael B Holmes
(74) *Attorney, Agent, or Firm* — Patterson + Sheridan, LLP

(57) ABSTRACT

Embodiments herein include a natural language computing system that provides a diagnosis for a participant in the conversation which indicates the likelihood that the participant exhibited a symptom of autism. To provide the diagnosis, the computing system includes a diagnosis system that performs a training process to generate a machine learning model which is then used to evaluate a textual representation of the conversation. For example, the diagnosis system may receive one or more examples of baseline conversations that exhibit symptoms of autisms and those that do not. The diagnosis system may annotate and the baseline conversations and identify features that are used to (Continued)

identify the symptoms of autism. The system generates a machine learning model that weights the features according to whether the identified features are, or are not, an indicator of autism.

7 Claims, 10 Drawing Sheets

(51) Int. Cl.
  *G06F 17/27* (2006.01)
  *G06F 17/30* (2006.01)
  *G06F 19/00* (2018.01)
  *G06N 99/00* (2010.01)
  *G10L 15/26* (2006.01)
  *G16H 50/20* (2018.01)

(52) U.S. Cl.
  CPC ........ *G06F 17/30976* (2013.01); *G06F 19/00* (2013.01); *G06N 7/005* (2013.01); *G06N 99/005* (2013.01); *G16H 50/20* (2018.01); *G10L 15/26* (2013.01)

(58) Field of Classification Search
  USPC .......................................................... 706/12
  See application file for complete search history.

(56) References Cited

U.S. PATENT DOCUMENTS

| | | | |
|---|---|---|---|
| 8,744,847 B2 | 6/2014 | Paul et al. | |
| 8,825,479 B2 | 9/2014 | Krishnan et al. | |
| 9,658,689 B2* | 5/2017 | Bedell, Jr. | G06F 3/013 |
| 9,727,936 B2* | 8/2017 | Ford | G06Q 10/10 |
| 9,773,195 B2* | 9/2017 | Feris | G06K 9/6269 |
| 9,794,550 B2* | 10/2017 | Khabiri | G02B 27/017 |
| 9,813,261 B2* | 11/2017 | Davies | H04L 12/6418 |
| 9,852,646 B2* | 12/2017 | Kozloski | G09B 5/02 |
| 9,886,572 B2* | 2/2018 | Goldberg | G06F 21/45 |
| 9,934,095 B2* | 4/2018 | Kim | G06F 11/1415 |
| 9,942,532 B2* | 4/2018 | Khabiri | G02B 27/017 |
| 9,953,217 B2* | 4/2018 | Feris | G06K 9/00369 |
| 9,996,217 B2* | 6/2018 | Kozloski | G06F 17/2217 |
| 10,035,555 B2* | 7/2018 | Erickson | B62J 27/00 |
| 10,066,391 B2* | 9/2018 | Kim | E04B 5/43 |
| 2009/0155751 A1 | 6/2009 | Paul et al. | |
| 2009/0191521 A1 | 7/2009 | Paul et al. | |
| 2009/0208913 A1 | 8/2009 | Xu et al. | |
| 2010/0332217 A1* | 12/2010 | Wintner | G06F 17/271 704/9 |
| 2013/0158986 A1* | 6/2013 | Wiles | G06F 17/279 704/9 |
| 2014/0255887 A1 | 9/2014 | Xu et al. | |
| 2014/0304200 A1* | 10/2014 | Wall | G06F 19/3418 706/12 |
| 2015/0286627 A1* | 10/2015 | Chang | G06F 17/2705 704/9 |

OTHER PUBLICATIONS

"Fuzzy cognitive map ensemble learning paradigm to solve classification problems: Application to autism identification", Elpiniki I. Papageorgiou, Arthi Kannappan, Applied Soft Computing, vol. 12 Issue 12, Dec. 2012, pp. 3798-3809.*

"An architecture for complex clinical question answering", Rodney D. Nielsen, James Masanz, Philip Ogren, Wayne Ward, James H. Martin, Guergana Savova, Martha Palmer, Proceeding IHI'10 Proceedings of the 1st ACM International Health Informatics Symposium, Arlington, Virgninia, Nov. 11-12, 2010, pp. 395-399.*

A Comparison of Machine Learning Algorithms for the Surveillance of Autism Spectrum Disorder Scott H Lee, Matthew J Maenner, Charles M Heilig, Author Affiliations: 1 Centers for Disease Control and Prevention, Atlanta, GA 2013 pp. 1-10.*

Exploring Autism Spectrum Disorders Using HLT Julia Parish-Morris, Mark Liberman, Neville Ryant, Christopher Cieri, Leila Bateman, Emily Ferguson, Robert T. Schultz, Proceedings of the 3rd Workshop on Computational Linguistics and Clinical Psychology: From Linguistic Signal to Clinical Reality, pp. 74-84, 2016.*

ScienceDirect Elsevier NeuroImage vol. 49, Issue 1, Jan. 1, 2010, pp. 44-56 Investigating the predictive value of whole-brain structural MR scans in autism: A pattern classification approach Christine Ecker et al.*

Use of Machine Learning to Identify Children with Autism and Their Motor Abnormalities Alessandro Crippa • Christian Salvatore • Paolo Perego • Sara Forti • Maria Nobile • Massimo Molteni • Isabella Castiglioni Published online: Feb. 5, 2015 Springer Science+Business Media New York 2015 pp. 2146-2156.*

U.S. Appl. No. 14/577,324, entitled Diagnosing Autism Spectrum Disorder Using Natural Processing, filed Dec. 19, 2014.

IBM "List of IBM Patents or Patent Applications Treated as Related".

* cited by examiner

DIAGNOSING AUTISM SPECTRUM DISORDER USING NATURAL LANGUAGE PROCESSING

CROSS-REFERENCE TO RELATED APPLICATIONS

This application is a continuation of co-pending U.S. patent application Ser. No. 14/577,324, filed Dec. 19, 2014. The aforementioned related patent application is herein incorporated by reference in its entirety.

BACKGROUND

The present invention relates to natural language processing, and more specifically, to evaluating textual conversation to identify symptoms of autism.

Natural language processing (NLP) is a field of computer science, artificial intelligence, and linguistics concerned with the interactions between computers and human languages. To interact with users, natural-language computing systems may use a corpus of documents that is parsed and annotated. For example, the computing system may identify an answer to a question based on models generated from annotations and/or the documents in the corpus.

SUMMARY

Embodiments described herein include a method for diagnosing autism. The method generates a machine learning model using training data comprising a first plurality of training examples, each example being a text of a conversation labeled as exhibiting at least one characteristic of autism. The method receives text of a conversation between a plurality of participants and evaluate the text of the conversation to generate features using natural language processing. The method evaluates the features using the ML model to determine a measure of probability that one of the plurality of participants falls on the autism spectrum.

BRIEF DESCRIPTION OF THE SEVERAL VIEWS OF THE DRAWINGS

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

Figure 1:
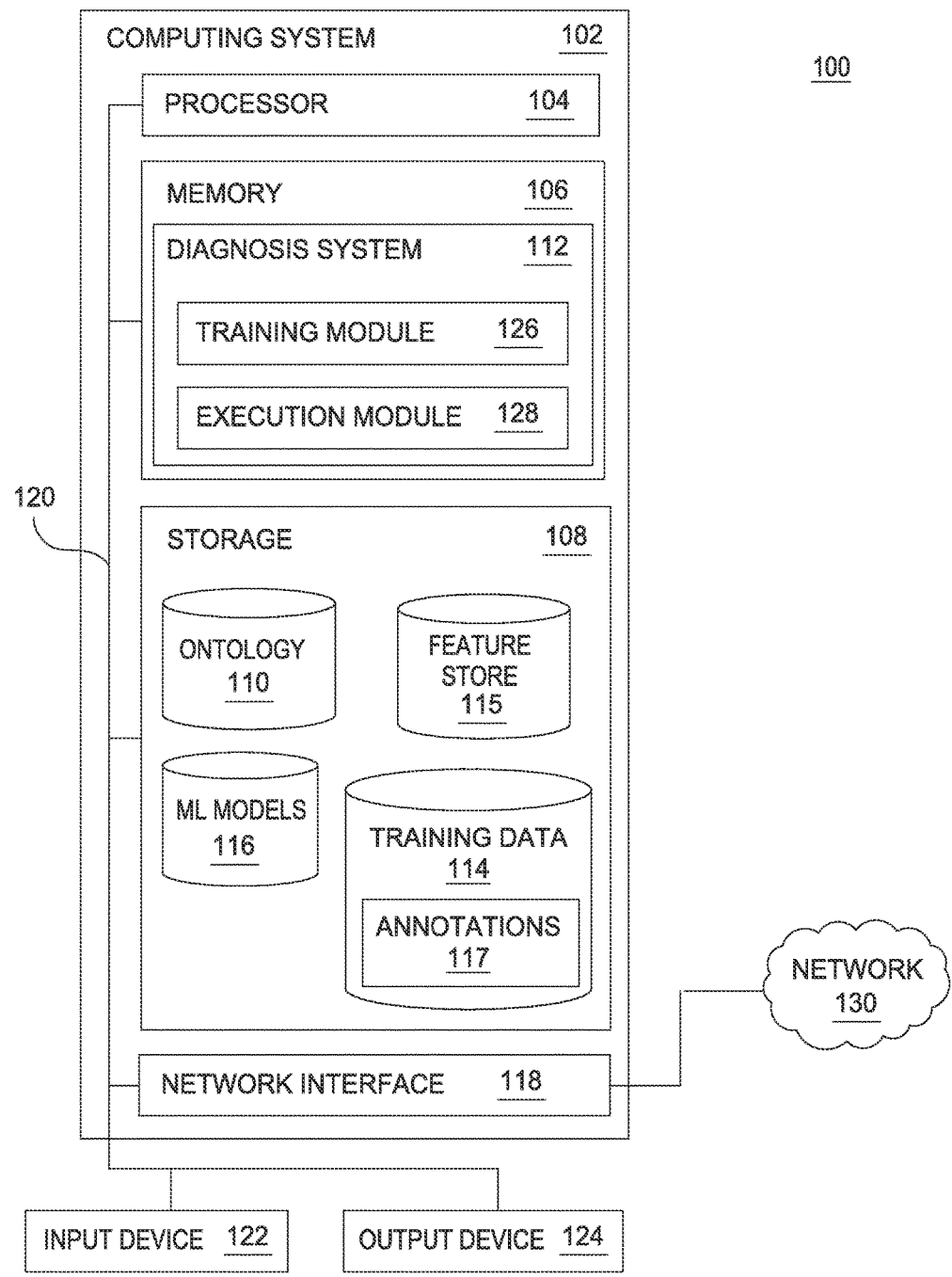
FIG. 1 is a block diagram illustrating a system for identifying symptoms of autism using textual conversations, according to one embodiment.

Embodiments herein describe techniques for identifying a characteristic of autism spectrum disorder using a computing system. Autism spectrum disorder ("ASD" or "autism") is a range of complex neurodevelopment disorders, characterized by social impairments, communication difficulties, and restricted, repetitive, and stereotyped patterns of behavior. A hallmark feature of autism is impaired social interaction.

In one embodiment, the computing system provides evaluates content of a conversation to determine a probability that the participant exhibits at least one characteristic (or symptom) of autism. To provide the measure of probability (e.g., a diagnosis), the computing system includes a diagnosis system that performs a training process using natural language process (NLP) techniques to generate a machine learning (ML) model which is then used to evaluate a textual representation of the conversation. To generate the model, the diagnosis system may evaluate conversations labeled as exhibiting a feature of autism as well as conversations that do not. Using an NLP application, the diagnosis system may annotate the baseline conversations and identify features that are used to identify the characteristics of autism. The application then generates the machine learning (ML) model which provides weights used to evaluate the results of performing natural language processing on other conversations.

For example, once trained, the diagnosis system can use the model to determine whether a participant in a conversation is exhibiting one or more characteristics of autism. For example, the system may process a textual representation of a conversation to identify one or more features. By evaluating the content and features derived by natural language processing, the diagnosis system determines a likelihood that a participant in a conversation evaluated using the model falls on the autism spectrum.

In another embodiment, the diagnosis system coaches an individual participating in a conversation by providing feedback about statements or patterns of behavior that may violate a social norm. For example, while the conversation is ongoing, the diagnosis system can evaluate a text version of the conversation to determine if the participant exhibits a feature of autism (e.g., violates a social norm). If so, the diagnosis system informs the participant. Using a chat room as an example, two (or more) parties may communicate using text statements. The system can monitor the statements made by a first participant and responses from other participant. If the diagnosis system determines that the content of messages exchanged between the first participant and others reflect or exhibit a characteristic of autism, a coaching application may generate a message notifying the first participant what particular characteristic was observed by the system—e.g., that the first participant is resisting or ignoring an attempt by another participant to change the topic of the conversation or that the first participant appeared to have not perceived an emotional aspect of a message from another participant. More generally, the coaching application may notify the first participant that the conversation is exhibiting a characteristic of autism. The coaching application may also suggest a corrective action to the participant. For example, if the participant fails to provide an appropriate response to an emotional statement made by another participant in the conversation (e.g., "My pet died yesterday"), the coaching application may suggest a sympathetic response to the participant (e.g., "I'm sorry to hear that"). Doing so both improves the quality of the interaction for the first participant as well as provides the first participant with the tools to better learn to recognize certain conversation patterns as well as to better recognize conversational cues when interacting with others.

FIG. 1 is a block diagram illustrating a networked system 100 for identifying characteristics of autism using conversation text, according to one embodiment. The networked system 100 includes a computing system 102, input device 122, and output device 124. The computing system 102 may also be connected to other computers via a network 130. In general, the network 130 may be a telecommunications network and/or a wide area network (WAN) such as the Internet.

The computing system 102 includes a processor 104 connected via a bus 120 to a memory 106, a network interface device 118, a storage 108, the input device 122, and the output device 124. Although shown as a single device, in other embodiments, the computing system 102 may include a network of distributed computing resources such as computing resources in a data center or in a cloud computing environment. The computing system 102 is generally under the control of an operating system (not shown) which can be any operating system capable of performing the functions recited herein. The processor 104 is representative of a single CPU, multiple CPUs, a single CPU having multiple processing cores, and the like. The memory 106 may include one or more random access memory modules that exist at multiple levels of a memory hierarchy and can range from high speed registers and caches to lower speed DRAM chips. The network interface device 118 may be any type of network communications device allowing the computing system 102 to communicate with other computing systems via network 130.

The storage 108 may be a persistent storage device. Although the storage 108 is shown as a single unit, the storage 108 may be a combination of fixed and/or removable storage devices, such as fixed disc drives, solid state drives, or removable memory cards. Memory 106 and storage 108 may be part of one virtual address space spanning multiple primary and secondary storage devices.

As shown, memory 106 contains a diagnosis system 112 which is configured to perform natural language processing on received text and process that text using a ML model 116. Diagnosis system 112 includes a training module 126 and an execution module 128. The training module 126 configures the diagnosis system 112 to identify symptoms, features, or patterns of behavior in the conversations of an individual which indicate a participant may fall on the autism spectrum. As described below, the training module 126 uses a set of training examples to generate the ML model 116 (e.g., a statistical model). In turn, the execution module 128 evaluates a conversation history of an individual to determine a measure of probability that the individual falls on the autism spectrum.

As shown, storage 108 contains ontology 110, training data 114, feature store 115, and ML models 116. Ontology 110 provides a structural framework for organizing information. In one embodiment, ontology 110 formally represents knowledge as a set of concepts within a domain, and the relationships between those concepts. Using ontology 110, the diagnosis system 112 can identify related topics in a conversation, identify when participants in a conversation are discussing different topics, identify patterns, and the like, which can be useful when identifying characteristics of autism.

Training data 114 is a body of information used by the training module 126 to configure the diagnosis system 112. In one embodiment, training data 114 includes a collection of conversations that exhibit a given characteristic, symptom or pattern of behavior of autism. The training data 114 may also include a collection of conversations labeled as not exhibiting such characteristics or features. In addition to stipulating whether the conversations do or do not exhibit characteristic of autism, the conversations may also be labeled to inform the diagnosis system what particular characteristic(s) or symptom of autism is exhibited in the conversation—e.g., a participant in the conversation ignores the attempts of another participant to change the topic of conversation or ignores an emotional statement but this is not a requirement. That is, by processing the training data, the diagnosis system 112 is able to identify the characteristics of autism automatically.

In this example, the training data 114 may include annotations 117 that provide metadata corresponding to the conversations. As the training data 114 is evaluated, training module 126 uses the annotations 117 to represent identified patterns, behaviors, topics of the conversations, and the like. In turn, the training module 126 may use the annotations 117 and the training data 114 to generate features saved in the feature store 115. During training, the ML model determines a set of weights reflecting how strongly a given feature of a conversation (alone or relative to others) should contribute to an overall likelihood that a participant to the conversation should be diagnosed as falling on the autism spectrum.

In one embodiment, the training module 126 is not informed of any particular feature of collections of conversations in the training data 114. Instead, each conversation is labeled as containing characteristics of autism and which do not. From the training data 114, the training module 126 generates ML model 116 using the annotations 117 and features 115 of the conversations. As noted, the ML model 116 may include a set of weights related to features (or groups of features) that can be used discriminate between conversations with a participant falling on the autism spectrum and conversations that do not. In turn, the execution module 128 evaluates a conversation to identify the features of that conversation evaluated by the model 116.

Although depicted as a database, ontology 110, training data 114, feature store 115, and ML models 116 may take any form sufficient to store data, including text files, xml data files, and the like. In one embodiment, the ontology 110 is part of the corpus 114. Although depicted as residing on the same computer, any combination of the diagnosis system 112, the ontology 110, training data 114, feature store 115, and ML models 116 may reside on the same or different computing systems.

The input device 122 may be any device that enables a user to communicate with the computing system 102. For example, a keyboard and/or a mouse may be used. The output device 124 may be any device for providing output to a user of the computing system 102. For example, the output device 124 may be any display screen (e.g., a standalone or wearable display device) or set of speakers. Although shown separately from the input device 122, the output device 124 and input device 122 may be combined. For example, a display screen with an integrated touch-screen.

Figure 2:
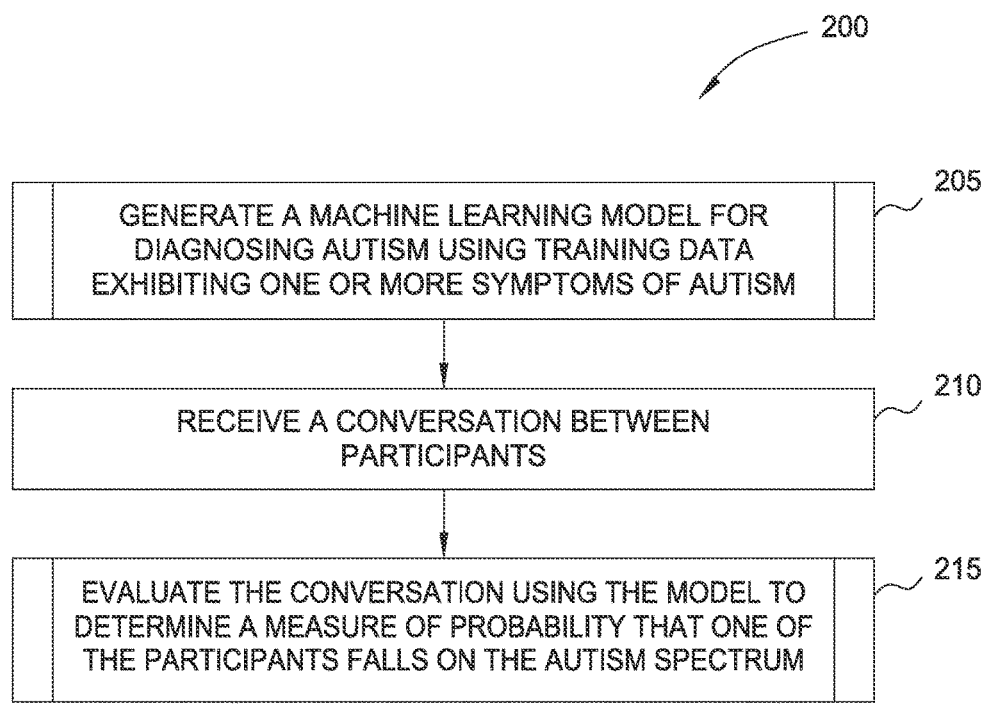
FIG. 2 illustrates a method for diagnosing autism by evaluating a textual conversation using a machine learning model, according to one embodiment.

FIG. 2 illustrates a flow chart 200 evaluating conversations to diagnose a conversation participant as falling on the autism spectrum, according to one embodiment. At step 205, the training module constructs an ML model to predict a likelihood that a conversation participant falls on the autism spectrum. For example, the training module receives textual conversations (i.e., training data) labeled as an example of conversations which exhibit characteristics of autism. The training data may also include conversations labeled as examples of conversations that do not exhibit a characteristic of autism. For example, difficulty in recognizing when a person is trying to change a topic of a conversation is one characteristic of autism. Similarly, a pattern of behavior of only discussing a specific topic is a sign of autism, especially when responses co-participant indicate a lack of interest in that topic. That is, a person on the autism spectrum may continue to talk about one subject despite another participant in the conversation attempting to change the topic of conversation. However, if participants in a conversation continually change topics, even where one person keeps returning to a given topic, it is not necessarily a sign of autism where other participants are generally engaged in the same topics at any given time. The training data may include baseline conversations that cover both of these examples.

By comparing the training examples, the training module identifies features about the conversations such as how many times the topic was changed, how many times a topic was mentioned, whether the participants were talking about the same topic, whether a question asked by one participant was ignored by the other participant, whether there was a gap in the conversation, etc. Some features (or combinations of features) may be predictive of autism. For example, just because a topic of the conversation changes, alone, is not a sign of autism. However, the training module may determine weights for this feature and other features, indicating how strongly changes in a topic of conversation (or how many changes in conversation) and whether participants follow changes or return to a prior topic, etc., should contribute to a likelihood that a given participant falls on the autism spectrum disorder. That is, the training module determines a set of weights for the features (and combination of features) to construct the ML model—e.g., features with greater weight correspond to a higher likelihood that the participant is exhibiting a characteristic of autism.

At step 210, the diagnosis system receives text content of a conversation to evaluate. In one embodiment, the conversation is a text document sent to the computing system 102 shown in FIG. 1 for processing. In other embodiments, the computing system 102 could receive an audio or video file and perform voice recognition techniques to generate a transcript of the conversation processed by the execution module. Furthermore, the diagnosis system may receive live conversations or pre-recorded conversations.

At step 215, the execution module evaluates the received conversation using the ML model to determine whether the participant exhibits one or more characteristics of autism. In one embodiment, the execution module uses a pipeline to process the received text and to generate features using similar natural language processing techniques as those used by the training module. These features can then be evaluated using the ML model. For example, if the conversation includes many features with high weights in the model (e.g., the features are indicative of multiple characteristics of autism), a diagnosis score is increased. In contrast, if the features identified by the execution module are assigned low weight in the model, the diagnosis score may be decreased (or is unchanged). Further, the ML model may consider the number of times a feature appears in the processed conversation—e.g., a feature with a low weight may have a large affect on the diagnosis score if it appears many times in the conversation. Generally, the execution module uses the ML model to determine if the features of the received conversation are more similar to the features of the training data that exhibits autism or more similar to the training data that does not exhibit autism.

Furthermore, the execution module may generate a diagnosis score for one or more participants in the conversation. For example, a user may specify which participants should be evaluated by the diagnosis system. Alternatively, the execution module may identify the different participants in the conversation (e.g., using user names, voice characteristics, formatting of the received data, and the like) and generate a diagnosis score for each participant separately.

The diagnosis score may indicate a measure of probability that a participant falls on the autism spectrum. In one embodiment, the diagnosis score may also include a score indicating a measure of confidence in the diagnosis score. For example, after processing the received conversation, the execution module may provide a percentage as the diagnosis score which indicates how certain the diagnosis system is that the person is autistic, or at least, exhibits one or more characteristics of autism. The confidence of the diagnosis score may vary based on any number of factors such as the adequacy of the training data, the number of features identified, the length of the received conversation, the quality or scope of the received conversation, and the like. For example, if the received conversation is only about one topic, a confidence score (which may be separate from the diagnosis score) may be lower than a conversation between a participant and a trained professional who is purposely changing the topic to test how the participant responds.

Figure 3:
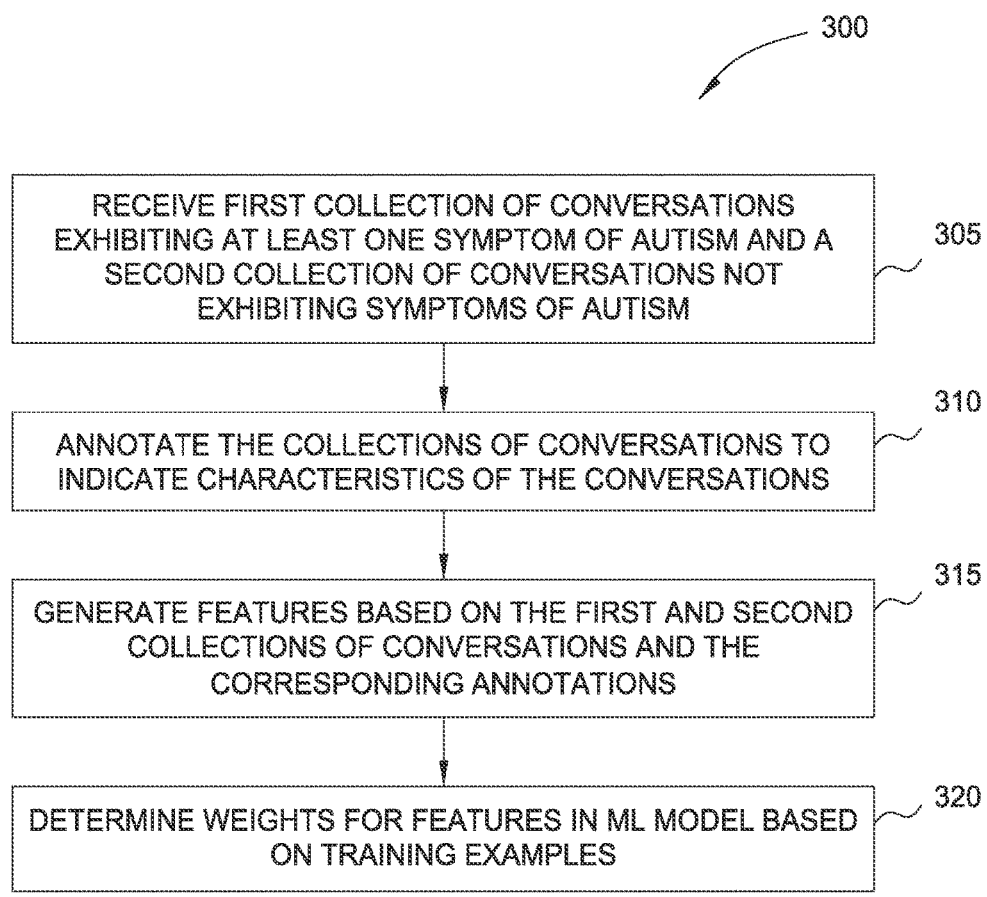
FIG. 3 illustrates a method for training a diagnosis system to diagnosis autism, according to one embodiment.

FIG. 3 illustrates a method 300 for training a diagnosis system to diagnosis autism, according to one embodiment disclosed herein. Method 300 generally corresponds to actions performed as part of step 205 of method 200. At step 305, the training module receives training data that includes text conversations labeled as exhibiting, or not exhibiting characteristics of autism. These baseline conversations may have been selected and labeled by subject matter experts (e.g., medical professionals specializing in behavioral analysis and neurological disorders). Thus, by evaluating features in the conversations using NLP techniques, the training module can develop a ML model that can classify other conversations as exhibiting the features, symptoms, or patterns of behavior related to autism reflected in the training examples.

At step 310, the training module includes an NLP application that annotates the baseline conversations to indicate a variety of features. For example, the NLP application may annotate with parts of speech, normalize and relate terms in the conversation using ontologies, identify clauses, phrases, sentences, sentence types, and other units of conversation as well structures and relationships among the units of conversation. The NLP application may also label units of conversation with topics, subjects, or concepts, measures of sentiment, measures of agreement, measures of shift in topic, etc. More generally, the NLP application may evaluate the baseline conversations to identify topics of conversation, which participants spoke each unit of conversation, emotional statements, questions asked by a participant, answers given in response to questions, and the like.

In one embodiment, the NLP application uses the ontology 110 shown in FIG. 1 to annotate the conversations. Because different words may relate to the same topic, the training module can use the ontology to determine if the participants are discussing the same topic or different topics. For example, one participant in a conversation may mention locomotives while another participant uses the term steam engine. Using the ontology and the NLP application, the training module can nonetheless determine that the participants are discussing the same topic—i.e., trains. Of course, this is only one use of the ontology, and in other embodiments, the ontology may be used to identify emotional statements, whether a participant answered a questions, and the like.

At step 315, the training module generates features using the baseline conversations and the annotations. The features may be patterns or behaviors identified in the baseline conversations. For example, the training module may provide annotations that indicate that a participant has discussed trains at ten different points in the conversation. Based on the annotations, the training module may identify a feature that indicates a subject was repeated 10 times by a participant. In this example, this feature identifies a pattern or behavior (e.g., a repeated topic) that is abstract from a particular topic which can then be used to describe a generic pattern or behavior (e.g., repeating a topic) rather than a specific pattern or behavior (e.g., talking about trains repeatedly). Another example includes a feature identifying a portion in the conversation where one participant mentions one subject (e.g., trains) a second participant then introduces a different subject (e.g., airplanes) which may be related or completely unrelated to the current topic. However, despite the attempts to change the subject, the participant continues to discuss the original subject (e.g., trains). In response, the training module generates a feature that indicates the participant resisted or ignored a change in the topic of conversation.

Other features that the training module can recognize using NLP techniques is one participant failing to respond to an emotional statement made by another participant, being unresponsive to questions, or unusual gaps in the conversation. Of course, the training module identifies features in the baseline conversations regardless of whether a given feature correlates to a characteristic or pattern of behavior related to autism. That is, the training module may identify features that are not indicators of autism.

At step 320, the training module generates the ML model by deriving a set of weights for features (and combination of features) identified in the training set by the NLP application. As mentioned, the training module may determine features and then weight these features using the ML model. For example, if the training module identifies a feature that indicates a participant dominated a conversation in a baseline conversation that does exhibit a characteristic of autism, but also found that same feature in a baseline conversation that does not exhibit a characteristic of autism, the training model may derive a low weight to the feature in the ML model. Conversely, if the training module identifies a feature in a baseline conversation that does exhibit a characteristic of autism that is not found in any of the baseline conversations that do not exhibit characteristics of autism, the training module may derive a greater weight to this feature in the model. Stated differently, if a particular feature identified using NLP techniques is found only (or predominantly) in the baseline conversations that do exhibit characteristics of autism, the training module determines this feature is likely a characteristic of autism and derives a greater weight to this feature relative to a feature that is found in both types of baseline conversations, or features found only in conversations that do not exhibit characteristics of autism. As an example, in both types of conversations, the training module may identify features where the topic of conversation changes, and thus, this feature is derived a lower weight. However, if a feature indicating that each time a participant introduced a new topic the other participant continued to discuss the same topic is only found in the baseline conversations exhibiting a characteristic of autism, this feature is given a greater weight.

In one embodiment, the training module may assign weights to individual features, as well as a combination of features, in the ML model which affect how the identified features affect the diagnosis score. For example, a feature that indicates a topic was changed in a conversation may be given a low weight, and thus, a smaller affect on the diagnosis score. However, this feature combined with another feature indicating that a participant ignored the change in topic may be given a greater weight. That is, the ML model may include weights for groups of features in addition to weights for individual features.

Advantageously, the training module does not need to be told what features are indicative of the characteristics of autism. Instead, by weighting features in the ML model, the training module independently determines the features that correspond to characteristics of autism and those that do not. Thus, the diagnosis system can identify the well known characteristics of autism (i.e., resisting topic changes, failing to answer questions, not recognizing emotional statements, etc.) as well as identify more subtle characteristics that may be overlooked by a medical professional or unknown to many medical professionals. For example, a given individual may not exhibit easily recognized characteristics but exhibit more subtle characteristics. If a medical professional is trained to recognize only the more well-known symptoms, the patient may be misdiagnosed. The diagnosis system, on the other hand, can identify all of the symptoms (assuming these symptoms are exhibited in the training data) and consider them as a whole using the weights in the ML model. For example, as discussed later, even if a participant in the conversation does not exhibit well-known symptoms, the ML model generated using method 300 may still accurately identify that the participant should be diagnosed as falling on the autism spectrum.

Figure 4:
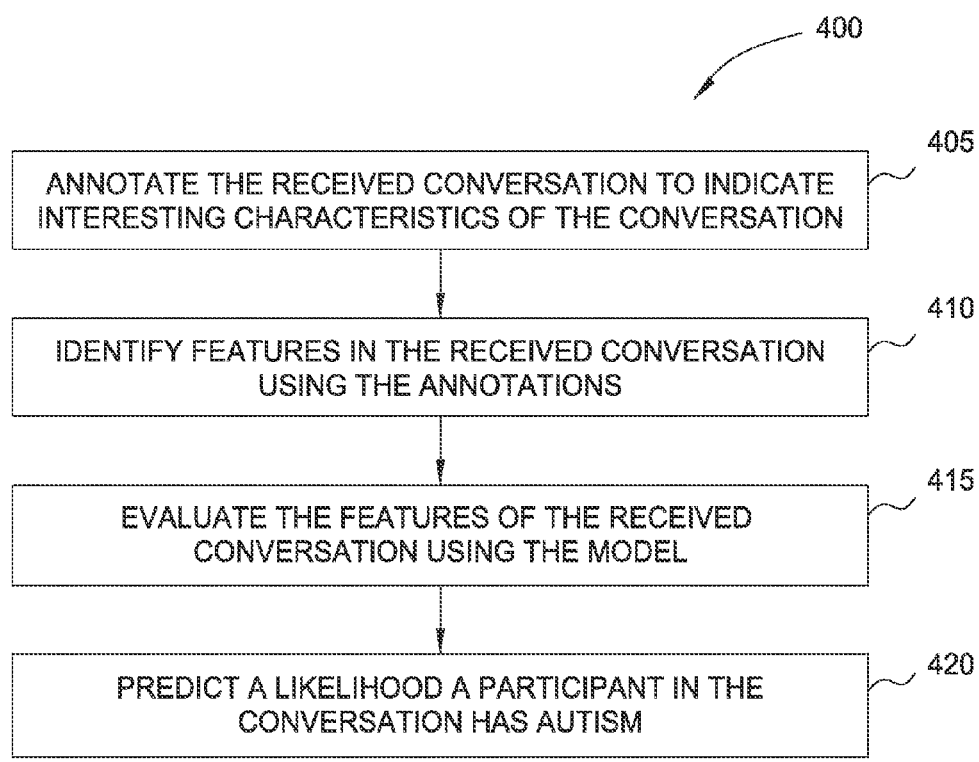
FIG. 4 illustrates a method for evaluating a textual conversation using the machine learning model, according to one embodiment.

FIG. 4 illustrates a method 400 for the ML module to evaluate a conversation, according to one embodiment. Note, method 400 generally corresponds to step 215 of method 200. At step 405, the execution module annotates the conversation received at step 210 of FIG. 2. Unlike the training data, the conversation is not labeled to indicate whether the conversation exhibits characteristics of autism. At step 410, the execution module annotates the conversation to identify metadata corresponding to the text. In one embodiment, the annotations and natural language processing generally corresponds to the same activity performed using the training examples (e.g., performed by the training module at step 310 of FIG. 3). For example, the execution module may use the same NLP techniques to process the conversation and identify topics of conversation, the participant who wrote or spoke the portion of the conversation, emotional statements, questions asked by a participant, answers given in response to questions, and the like. Additionally, the execution module may use the ontology 110 shown in FIG. 1 to identify terms corresponding to the same topic, identify emotional statements, etc.

At step 410, the execution module identifies features in the conversations using the annotations. Generally, the NLP techniques used by the training module to identify the features in the baseline conversations may also be used here. The execution module using NLP techniques to identify features in the text of the received conversation. Like the training module, the execution module may search for any pattern or behavior as a feature without regards to whether these features are related to autism. As such, any NLP techniques may be used to identify features. However, one advantage of using NLP techniques to diagnose autism is that these techniques excel at identifying patterns and behaviors (i.e., features) in text. Using the embodiments described herein, the execution module can identify the features in the received text and then use the ML model to determine the diagnosis score, based on the specific features present in a conversation At step 415, the execution module processes the features identified from the received conversation using the ML model. Specifically, ML model applies the weights learned during training to the features and combinations of features to determine a diagnosis score that the conversation has a participant with autism. Because the weights in the ML model are generated using the baseline conversations in method 300, by using the ML model, the execution module determines whether the patterns and behaviors in the received conversation have more in common with the patterns and behaviors in the baseline conversation that do exhibit characteristics of autism, or the patterns and behaviors in the baseline conversations that do not exhibit characteristics of autism. More specifically, the weights of the ML model determine how the observed features (and combinations of features) should contribute to a likelihood that a participant has autism.

In one embodiment, if a feature identified at step 410 does not have a corresponding weight in the ML model, the execution module may ignore the feature. That is, the feature does not contribute to the likelihood. Alternatively, the execution module may compare the feature to other features that are assigned weights in the ML model and assign the average of those weights to the feature that are most similar.

At step 420, the execution module determines the likelihood a participant in the conversation is autistic, or at least, that the conversation pattern exhibits a characteristic of autism. In one embodiment, the execution module may combine the weights identified at step 415 to determine a diagnosis score—e.g., the features and weights yield a diagnosis score. Because the ML model may assign greater weight to features that are found only in the baseline conversations that exhibit characteristics of autism, if the features identified at step 410 are the same as these features, the combined weight and diagnosis score increases. Conversely, if the features identified at step 410 are the same as features that are found in both types of baseline conversations or only in the baseline conversations that do not exhibit autism, the combined weight and diagnosis score decreases.

In one embodiment, the diagnosis score indicates a likelihood a participant in the conversation falls on the autism spectrum. This percentage may be directly correlated with the combined weight. Stated differently, as more features (or combination of features) identified at step 410 match the features identified by method 300 as corresponding to the characteristics of autism, the combined weight of the features increases. The greater the combined weight, then the higher the percentage of the diagnosis score indicating that the participant has autism. Additionally, the percentage and the combined weight may consider that some features (or characteristics of autism) are stronger indicators of autism than other features (or characteristics). For example, if the training module processed five baseline conversations that all exhibited characteristics of autism, the ML model may assign greater weight to a feature identified in all five of these conversations (assuming that feature was not also found in the baseline conversations that do not exhibit autism) relative to a feature identified in only one or two of the conversations. Thus, if at step 410, the execution module identifies the same feature in the received conversation that was in all five baseline conversations, that feature is given a greater weight and would increase the percentage score and the confidence in the diagnosis relative to identifying a feature found in only one or two of the baseline conversations exhibiting signs of autism. Nonetheless, a participant who may not exhibit the primary or well-known characteristics of autism (which may be assigned the greatest weight in the ML model) may still be correctly diagnosed if he exhibits many of the lesser known characteristics (which may have lower weights).

In one embodiment, the diagnosis score may be used as the primary diagnosis for a patient in order to determine a treatment plan. Alternatively, the diagnosis score may be used to supplement or provide a second opinion for a patient that has already been diagnosed by a medical professional. In yet another example, the diagnosis score may be used to screen patients to determine whether they should then see a specialist in the field of ASD. For instance, only the patients that have a diagnosis score in a predetermined range are referred to a specialist while those outside of this range are not.

In one embodiment, in addition to providing the diagnosis score, the execution model may generate a confidence score that provides an estimated accuracy of the diagnosis score independent of the diagnosis score. For example, as the length of the conversation increases, the confidence score may increase. Or the confidence score may change according to the number of features identified at step 410. Stated differently, the confidence score depends on the amount of data and the quality of the data in the received conversation. If the execution module was not able to identify many features, regardless of how those features are weighted, the execution module may decreases the confidence score indicating the sample size (i.e., the text of the conversation) was too small or the type of conversation was not well suited for performing the analysis described herein.

Furthermore, although the embodiments described above are explained in the context of autism, the diagnosis system may also be used to identify other medical disorders (e.g., neurodevelopment disorders, social disorders, mental disorders, etc.) that can be diagnosed by ingesting and processing text. That is, instead of receiving baseline conversations that exhibit signs of autism, the training module can generate a ML models for a different disorder by receiving baseline conversations that do (and do not) exhibit characteristics of the disorder. These ML models may be used as described above to process conversations with participants that have not yet been diagnosed.

Figure 5:
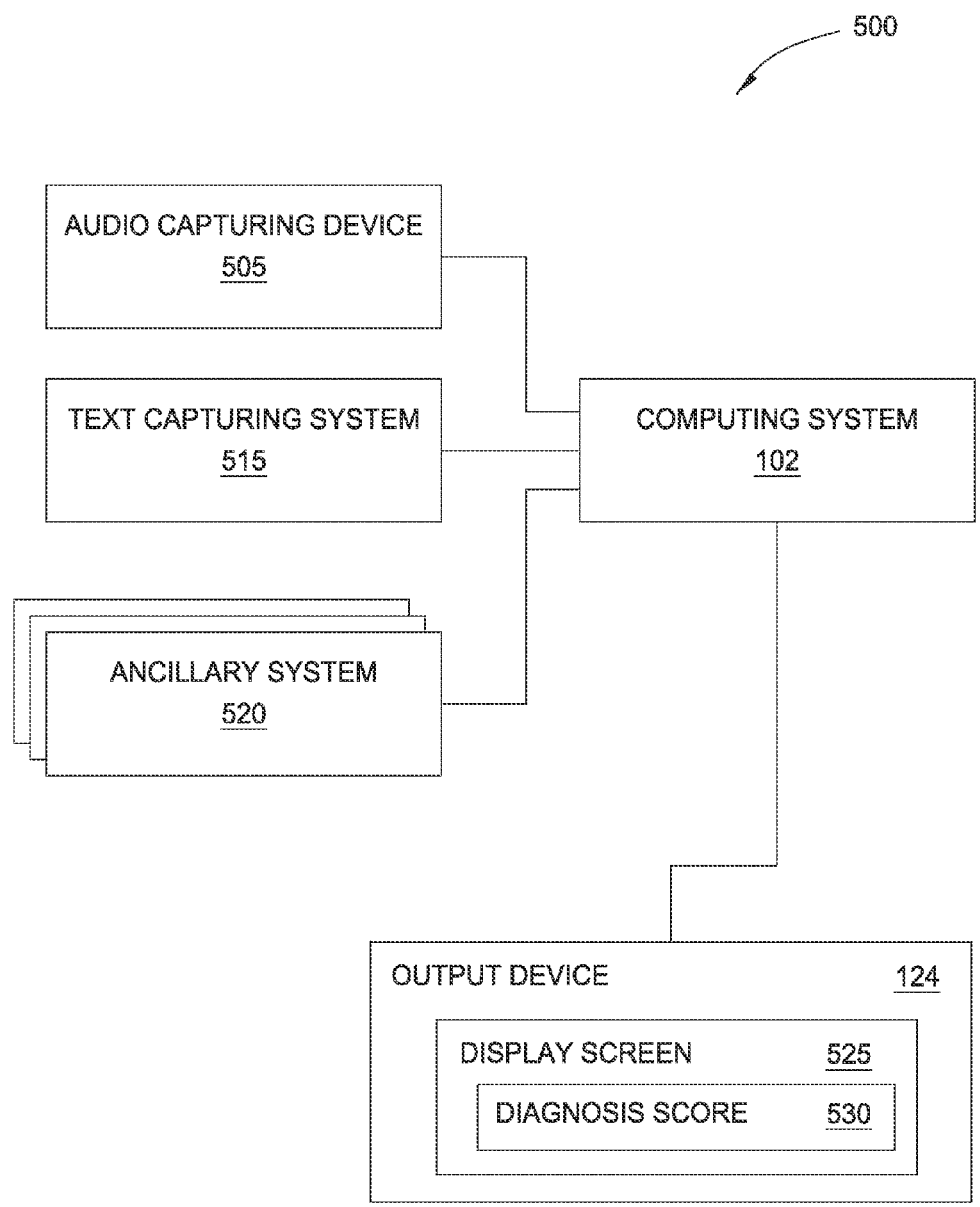
FIG. 5 is a block diagram illustrating a system for providing a diagnosis from evaluating a textual conversation, according to one embodiment.

FIG. 5 is a block diagram illustrating a system 500 for providing a diagnosis from evaluating a textual conversation, according to one embodiment disclosed herein. As shown, system 500 includes audio capturing device 505, text capturing device 510, ancillary systems 515, computing device 102, and output device 124. The audio capturing device 505 may be a video or audio recorder that captures a conversation between two or more participants—e.g., camcorder, tape recorder, voice recognition system, etc. In one embodiment, audio capturing device 505 includes an audio translation module that translates the captured audio into a textual representation of the conversation which is then transmitted to the computing system 102 for diagnosis. In other embodiments, this audio to text translation is performed on the computing system 102.

The text capturing system 515 may be chat monitor, short message service (SMS) monitor, instant messaging system monitor, and the like that captures the conversation between two people that may occur using electronic devices—e.g., computing, mobile phone, tablet, etc. The text capturing system 515 compiles the conversation between two or more participants over the electronic devices and transmits the conversation to the computing system 102 for diagnosis as described above.

In addition to monitoring textual conversations, the computing system 102 may also consider information provided by the ancillary systems 520 when diagnosing a participant in a received conversation. For example, the ancillary systems 520 may include a video detection system that monitors the eyes movements of the participants during the conversation. Because some signs of autism cannot be captured in textual conversations—e.g., repetitive movements, poor eye contact, or gaps in conversations (assuming the audio capturing device or text capturing system do not provide timestamps with the textual conversation)—the ancillary systems 520 may provide this information to the computing system 102 which can use the information to alter the diagnosis score generated using the ML model. For example, one ancillary system 520 may track the body movements of the participant while another system 520 determines if there are gaps in the conversation. In this manner, the natural language processing performed by the computing system 102 may be combined with other detection systems for identifying additional characteristics of autism.

As shown, output device 124 includes a display screen 525 which display the diagnosis score 530 generated by the execution module on the computing system 102. In addition to outputting the diagnosis score 530, the display screen 525 may also output the confidence score (if calculated) as well as a list of the features found in the conversation that were weighted the heaviest by the ML model. In this manner, the person viewing the screen 525 can see the basis of the diagnosis—i.e., which features were identified as being characteristics of autism. Instead of using the display screen 525, in another embodiment, the diagnosis score may be given using audio means—e.g., speakers, headphones, etc.

Figure 6:
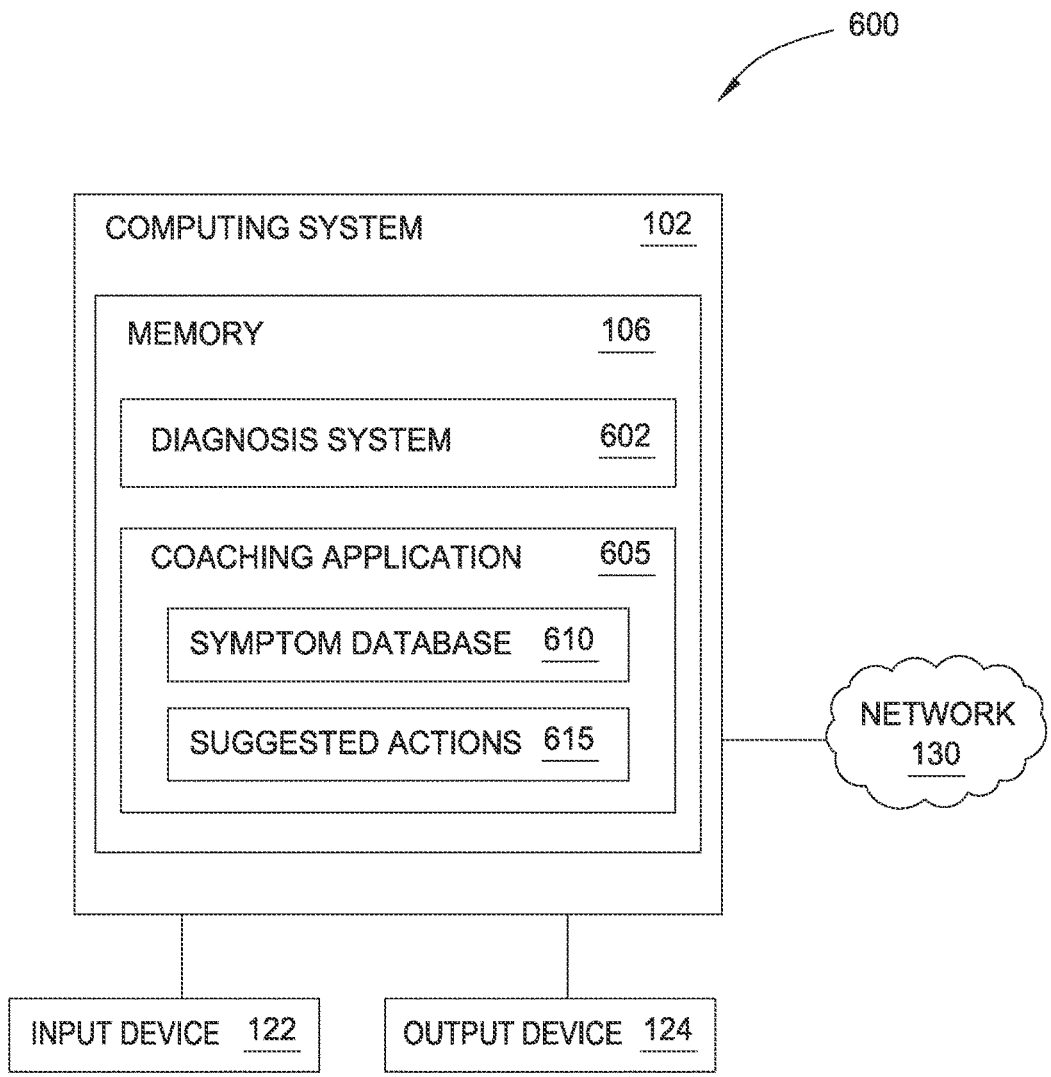
FIG. 6 is a block diagram illustrating a system for providing coaching to a participant in a conversation exhibiting a symptom of autism, according to one embodiment.

FIG. 6 is a block diagram illustrating a system 600 for coaching a participant in a conversation regarding certain conversation pattern, according to one embodiment. System 600 includes computing system 102, network 130, input device 122, and output device 124 which were described in detail in FIG. 1. The computing system 102 includes memory 106 and may include storage elements such as an ontology, feature store, training data, and ML models (not shown) to perform and execute a diagnosis system 602.

Memory 106 also includes coaching application 605 which monitors a conversation between at least two participants and provides a notice to a participant when he exhibits a characteristic of autism during the conversation. For example, the diagnosis system 602 may detect that the participant resisted or ignored an attempt by another participant to change the topic of conversation, failed to answer a question, or did not recognize an emotional statement. In response, the coaching application 605 causes the computing system 102 to output the notice to the participant which identifies his mistake. For example, if the conversation is occurring in a chat room, the coaching application 605 may launch a pop-up that says "John is trying to change the subject from trains to planes." The participant can then use this notice to modify or adapt his behavior. In one embodiment, in addition to providing the notice, coaching application 605 suggests a socially appropriate action to the participant. Continuing the example of above, the application 605 may include in the pop-up the statement: "Suggestion: Tell John something that interests you about planes." Thus, the coaching application 605 can help the participant to recognize conversation patterns that may not conform well with expected social norms. Note, the coaching application 605 may be used to notify conversation participants of certain disruptive patterns of conversation.

The coaching application 605 includes a symptom database 610 that is used to identify symptoms using information provided by the diagnosis system 602. Note, diagnosis system 602 generally corresponds to the diagnosis system 112 in FIG. 1. Thus, diagnosis system 602 includes an execution module used to identify conversation patterns. Once a ML model determines to classify a conversation as exhibiting a characteristic of autism, the coaching application 605 may correlate a sequence of features identified by the diagnosis system with symptom database 610 to provide an explanation of that symptom when notifying the participant. Stated differently, the symptom database 610 helps the coaching application 605 to translate the features identified by the diagnosis system 602 into a statement that can be understood by the participant.

The coaching application 605 also includes suggested actions 615 which the application 605 can suggest to the participant. This list may include different actions for different symptoms as well as different contexts. For example, the coaching application 605 may suggest a different suggested action when the participant fails to answer a question then when the participant fails to show sympathy.

Although FIG. 6 illustrates the diagnosis system 602 and the coaching application 605 being located on the same computing system 102, this is not a requirement. In other embodiments these applications may be hosted on different computing systems—e.g., the diagnosis system 602 may be located on computers in a data center (e.g., a cloud service provider) while the coaching application 605 is located on a local computing device of one of the participants.

While, the coaching application may be used to notify a conversation participant that the conversation is exhibiting characteristics generally related to certain autistic patterns of communication, particularly characteristics where an individual with autism has difficulty recognizing social cues or norms about topics, responses, gaps, etc., the coaching application is not limited to such. For example, the diagnosis system 602 and coaching application 605 may be used to detect and inform a participant that he is exhibiting a characteristic of other medical disorders, whether mental or social. Further, the diagnosis system 602 and coaching application 605 may be used to identify and help individuals adjust communication patterns arising out of inexperience or poor social habits or skills. For example, a participant just learning a language (e.g., English) may miss social cues that a person with more experience would recognize. The diagnosis system 602 can be configured to recognize these social cues while the coaching application 605 notifies the participant when his behavior does not conform to a social norm. For example, the participant may not recognize that the other participant is trying to end the conversation. In response, the coaching application 605 notifies the participant that statements that seek to extend the conversation may violate a social norm. Thus, although the examples herein disclose configuring the diagnosis system 602 and coaching application 605 for detecting characteristics of autism, these applications may also be used to detect a variety of communication patterns regardless of whether a conversation participant falls within the autism spectrum, does not know or does not have the skills to conform to the social norm, or because he has developed poor social habits.

Figure 7:
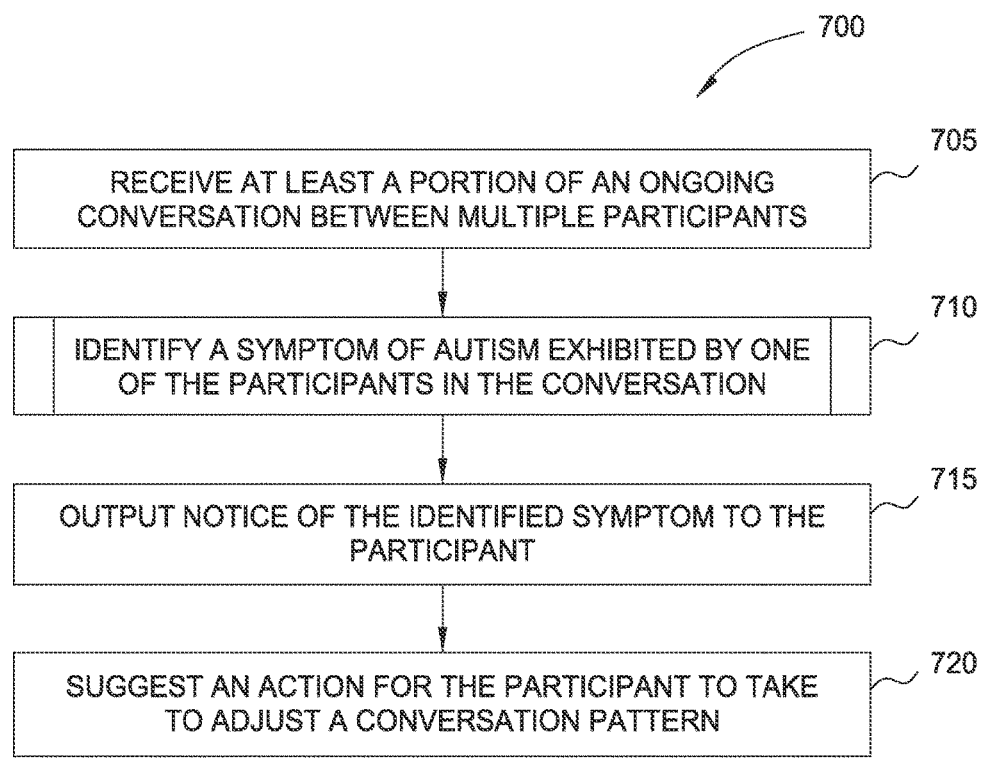
FIG. 7 illustrates a method for coaching a person exhibiting a symptom of autism, according to one embodiment.

FIG. 7 illustrates a flow chart 700 for coaching a participant in a conversation regarding certain conversation patterns, according to one embodiment. At step 705, the diagnosis system receives text of a conversation between multiple participants. In one embodiment, the conversation is an ongoing conversation between the participants. For example, the textual conversation may be captured from SMS messages, instant messaging applications, emails, streaming audio or video data, and the like. Even though the conversation is still ongoing, the diagnosis system may receive data that is somewhat delayed. For example, it may take a few moments for the audio being captured to be translated into text or to be received at the diagnosis system. Nonetheless, in this situation, the coaching application is still considered as providing coaching in real time for the ongoing conversation.

The diagnosis system may receive portions of the ongoing conversation in chunks or batches. For example, each time a participant sends a SMS message, the message may also be forwarded to the diagnosis system. To forward the messages, the computing device that is used by one of the participants in the conversation may include a local application that monitors the conversation and forwards updates to the diagnosis system. In another example, a chat room server may include an application where every time a participant in the conversation sends a chat message to the other participants, the application forwards the updated message to the diagnosis system. In this manner, the diagnosis system can receive real time data which can be used to provide up-to-date feedback to a participant who is exhibiting a characteristic of autism.

In one embodiment, the diagnosis system may process only a portion of the conversation—e.g., only the last five minutes of the conversation or the last five SMS messages or chat entries. Because the coaching application may be focused on giving feedback regarding participants' current behavior in the conversation, in this example, the application evaluates the recent data and excludes prior portions of the conversation.

At step 710, the diagnosis system identifies characteristics generally related to certain autistic patterns of communication, being exhibited by a participant in the conversation. Stated generally, the diagnosis system can identify when a participant violates a social norm; particularly norms for conversations some individuals on the autism spectrum have difficulty recognizing or formulating a socially appropriate response. In one embodiment, the diagnosis system uses the method 200 illustrated in FIG. 2 to train a model that can accurately identify conversations which exhibit such characteristics. For example, the diagnosis system may first use a training pipeline that receives baseline conversations labeled as exhibiting (or not exhibiting) signs of autism processed to identify features (e.g., patterns or behaviors) in the conversations. As shown in more detail in FIG. 3, the diagnosis system compares the identified features in the baseline conversations to develop weights for a ML model. Using the ML model, the diagnosis system can then process the ongoing conversation received at step 705 and identify features that correspond to characteristics of autism.

However, method 200 is only one example of a diagnosis system that may be used by the coaching application. While the discussion above uses NLP techniques to label features of conversations and ML techniques to build a model that can classify a conversation based on features of that conversation—other ML techniques could be used.

In one embodiment, the diagnosis system includes a threshold for taking action based on a probability in the determinations made by the coaching application in evaluating an ongoing conversation. After processing the text of the ongoing application, the diagnosis system may generate a measure of probability whether the conversation pattern of a participant exhibits a characteristic of autism (or violates a social norm). Moreover, the coaching application may also reevaluate previously received portions of the conversation when generating the predictive score (that is, the features of the conversation generated by the NLP model nay be updated, revised, or augmented with each received unit of conversation). For example assume a first participant is ignoring a second participant's attempt to change the topic of conversation. In such a case, the diagnosis system could monitor a most recent SMS message along with previously sent and received messages to determine what the previous topic of the conversation was, whether the second participant attempted to change the topic of conversation, and whether the first participant is continuing to discuss the original topic. In such a case, the diagnosis system may determine that the conversation is not exhibiting signs of autism, but continue to evaluate new portions of the conversation in context of the previous portions to determine if the predictive score now satisfies the threshold—i.e., the application indicates that the conversation exhibits a characteristic of autism.

At step 715, the diagnosis system informs the coaching application that a characteristic of autism was identified. In response, the coaching application outputs a notice of the identified symptom to the participant. As mentioned above, the coaching application may use the symptom database to provide a description of the symptom to the participant. That is, the database may be used to translate the information provided by the diagnosis system into a grammatical statement which is displayed to the participant. For example, the notice may be displayed in a display screen of a computing device used to conduct the conversation (e.g., a GUI for a chat or SMS messaging application). In other embodiments, the notice could provide tactile or audio feedback. For example, mobile phone capturing the audio of a conversation could vibrate or beep when the conversation exhibits a given pattern of communication recognized by the coaching application. Further, different vibration patterns or beeps may be used to indicate what characteristic of autism the participant exhibited—e.g., one beep correspond to a lengthy gap in the conversation, while two beeps correspond to resisting the attempts of another participant to change the topic. In another example, the coaching application may output an audio message via an earpiece being worn by the participant or display a message on a display device worn on the head of the participant.

At step 720, the coaching application suggests an action for the participant which remedies or mitigates a negative impact caused by exhibiting the characteristic of autism. Stated differently, the behavior of the participant detected by the diagnosis system may be a socially awkward or inconsistent with accepted social norms or rules of etiquette typically followed during a conversation. To mitigate the effects of this behavior on the other participants in the conversation, the coaching application suggests an action to the participant which conforms the participant's behavior to the social norm. Using the list of suggested action discussed above, the coaching application may identify an action that corresponds to the behavior of the participants or the particular characteristic of autism being exhibited. For example, if the participant failed to recognize the other participant is trying to end the conversation, the coaching application may suggest a phrase that is typically used to end a conversation such as "it was good to talk to you, let's chat again soon." Or if the participant does not respond to an emotional statement made by another participant, the coaching application could suggest that the participant use a sympathetic statement such as "that's a terrible thing to have happen."

In addition to suggesting statements that could be written or spoken to the other participants, the coaching application could also suggest non-verbal or non-textual forms of communication, actions or behaviors to show sympathy, making periodic eye contact, or waving goodbye to end a conversation. These suggestions may be made in combination with other statements suggested by the coaching application.

Although discussed in the context on an ongoing conversation between participants, method 700 is not limited to such. In other embodiments, the diagnosis system and coaching application may review completed conversations. For example, the diagnosis system could receive all the chat or SMS messages sent and received by a user throughout the day. The diagnosis system can process these conversations and identify passages that exhibit signs of autism or violate social norms. The coaching application can notify the user and provide an explanation of how the conversation violated a social norm. This permits the participant to review the conversations and hopefully learn to better recognize certain social cues.

Figure 8:
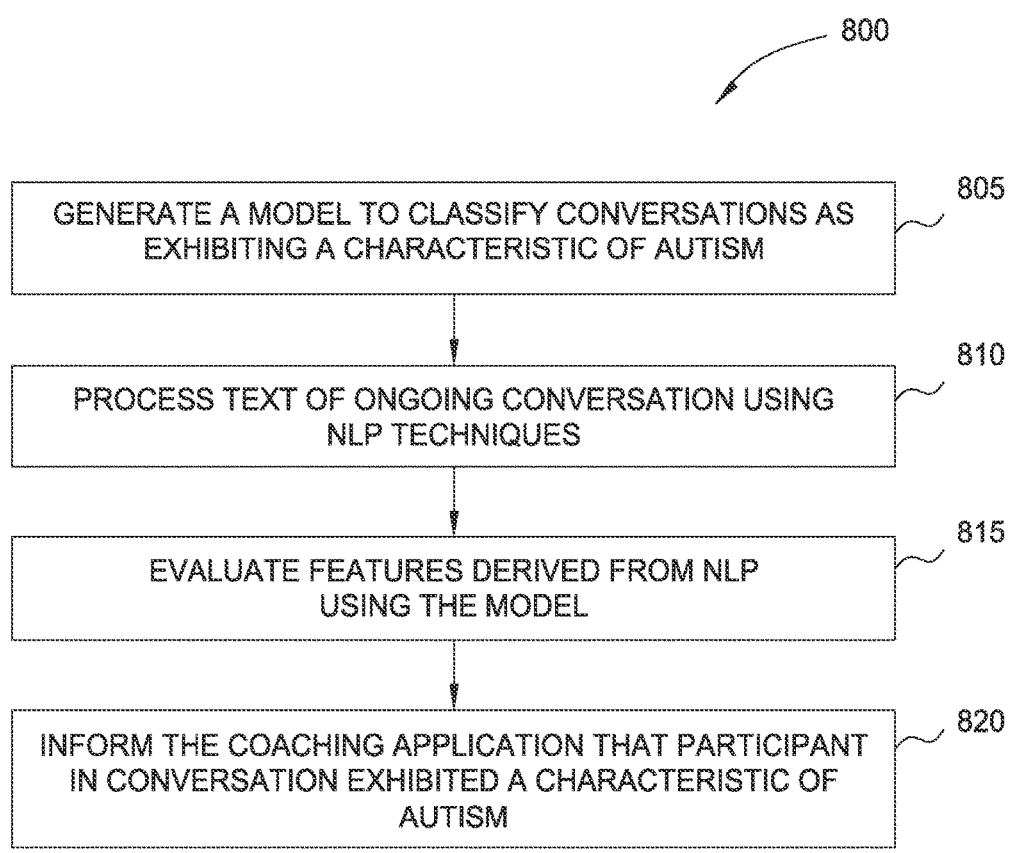
FIG. 8 illustrates a method for training a diagnosis system to identify a symptom of autism being exhibited in a conversation, according to one embodiment.

FIG. 8 illustrates a flow chart 800 for identifying characteristic of autism in a conversation. In one embodiment, flow chart 800 is a flow for performing step 710 shown in FIG. 7 where the diagnosis system is used to identify a characteristic of autism in a conversation. However, method 800 is just one example of a suitable NLP technique for detecting characteristics of autism. In other example, a NLP technique that does not require a ML model or a training process may be used.

At step 805, the diagnosis system generates a ML model to recognize a characteristic of autism which violates a social norm. In one embodiment, the ML model may be generated using one or more baseline conversations that do and do not exhibit characteristics of autism. Generating such ML models was disclosed in method 300 of FIG. 3 and will not be described in detail here.

At step 810, the diagnosis system processes the text of the ongoing conversation. The text may be sent to the diagnosis system in batches or a sequence of updates. These updates may be sent by chat application, SMS applications, or audio capturing devices that record the conversation.

At step 815, the diagnosis system evaluates the processed text using the model. In one embodiment, the diagnosis system uses method 400 in FIG. 4 to generate features which are then weighted using the ML model. The diagnosis system may compare a predictive score to a threshold to determine whether a particular portion of the conversation exhibits a characteristic of autism. If so, at step 820, the diagnosis system transmits information about the characteristic to the coaching application. In one embodiment, the diagnosis system may provide a code to the coaching application which it then translates into a description of the symptom using the symptom database. In addition, the diagnosis system may provide other information such as the topic of the conversation, the names (or user names) of the different speakers in the conversation, the text of the conversation that includes the characteristic of autism, and the like. The coaching application can use this information when providing the notice to the participant. Alternatively, the diagnosis system, rather than the coaching application, may generate the statement that explains to the participant how his behavior corresponds to a characteristic of autism. The coaching application would then output the statement provided by the diagnosis system in the notice to the participant.

Figure 9A:
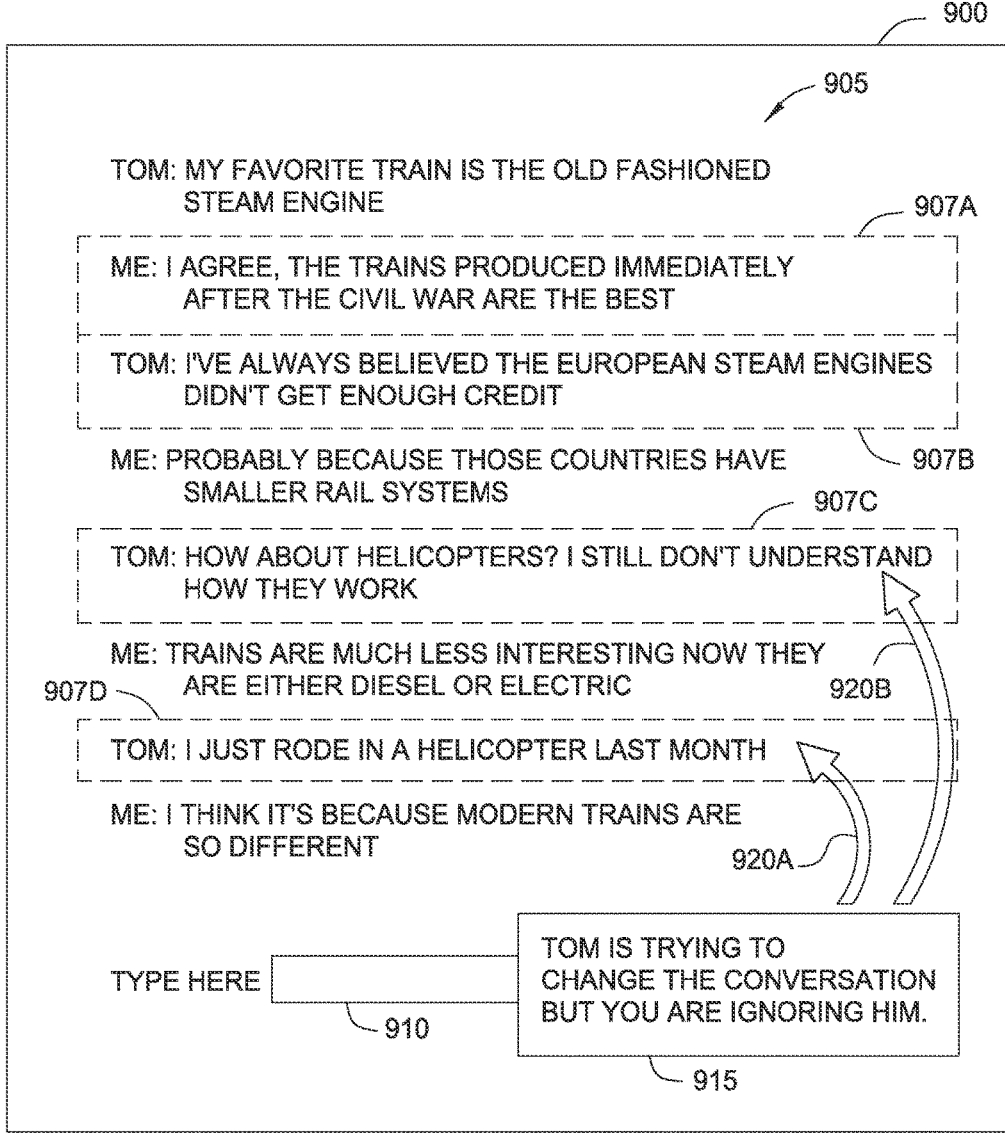
FIGS. 9A and 9B illustrate graphical user interfaces coaching a person exhibiting a symptom of autism during a conversation, according to embodiments.
Figure 9B:
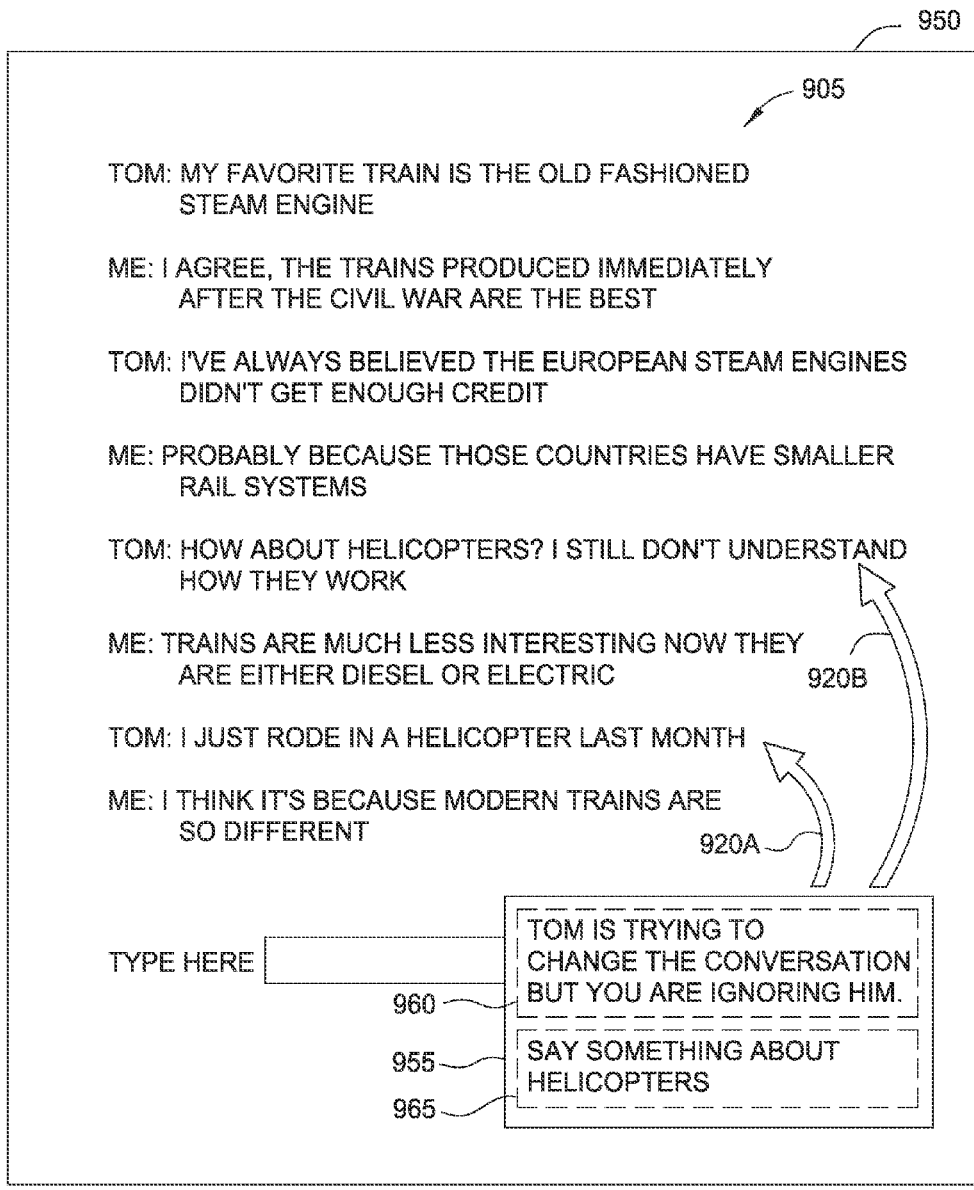

FIGS. 9A and 9B illustrate a GUI 900 for coaching a person regarding certain patterns of conversation, according to embodiments. As shown in FIG. 9A, GUI 900 includes a conversation 905 between two participants using a chat application. As the conversation 905 progresses, the application sends the chat portions 907 to the diagnosis system as the participants transmit the portions 907 to each other. Stated differently, when a participant types a message into region 910 and sends the message to other participants, the chat application forwards the message to the diagnosis system. Alternatively, the chat application may wait until multiple messages are sent before forwarding the corresponding portions 907 to the diagnosis system.

As discussed, the diagnosis system processes the text of the conversation 905 to predict whether the conversation exhibits a characteristic or pattern of behavior characteristic of autism. As shown, the diagnosis system identifies that one of the participants (the user labeled "Me") is ignoring an attempt by another participant (the user labeled "Tom") to change the topic of conversation. For example, at portions 907A and 907B both participants are discussing the same topic—i.e., trains. However, at portions 907C and 907D Tom makes repeated attempts to discuss a different subject—i.e., helicopters—which is ignored either consciously or unconsciously by the other participant. In response, the coaching application outputs for display a notice 915 which includes a statement describing that the participant labeled "Me" has failed to recognize that the other participant is trying to change the subject. The notice 915 is shown as a pop-up that overlays a portion of the GUI 900. However, in other embodiments, the notice 915 may be in line with elements already being displayed in the GUI 900. Furthermore, the coaching application may also output an audio prompt that accompanies the notice 915 (e.g., a vibration or ding) to attract the participant's attention. In one embodiment, instead of the notice 915 including a statement describing the behavior of the participant, the coaching application may highlight portions 907C and 907D to capture the attention of the user so he will recognize that the other participant is attempting to change the topic. In addition, the coaching application may cause the new topic (e.g., the word "helicopter") to begin flashing or change colors in the GUI 900 in order to provide notice to the user that he has violated a social norm.

In addition to the statement, the coaching application outputs for display arrows 920 which point to the portions 907C and 907D in the conversation 905 that caused the diagnosis system to determine the participant is exhibiting a characteristic of autism. The arrows 920 provide additional feedback to the participant so he can quickly identify his mistake as well as potentially remedy the situation—e.g., begin discussing helicopters instead of trains.

FIG. 9B illustrates a GUI 950 with the same conversation 905 as the one illustrated in FIG. 9A. In addition to identifying symptoms or pattern of behavior exhibited by the messages from the participant, GUI 950 includes a notice 955 that identifies a general statement of the symptom 960 as well as an action 965. That is, the coaching application provides a suggestion for adjusting the participant's behavior. In this example, the coaching application suggests that the participant change the topic to follow the topic being introduced by the other participant (Tom). The action 965 suggested by the coaching application may vary based on the particular symptom or pattern of behavior identified by the diagnosis system, the context of the conversation, subject matter of the conversation, the communication medium in which the conversation is taking place (e.g., via chat message, email, in-person, etc), and the like.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the preceding, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the preceding aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., the diagnosis systems 112 or 602) or related data available in the cloud. For example, the diagnosis system could execute on a computing system in the cloud and identify characteristics of autism. In such a case, the diagnosis system could receive the textual conversations and store the results of processing those conversations at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method for evaluating a textual conversation, comprising:
    generating a machine learning (ML) model using training data comprising a first plurality of training examples, each example being a text of a conversation labeled as exhibiting at least one characteristic of autism;
    receiving text of an ongoing conversation between a plurality of participants;
    annotating the text of the conversation using natural language processing;
    identifying features in the conversation using the annotations;
    evaluating the features using the ML model to determine a measure of probability that a first one of the plurality of participants in the conversation falls on the autism spectrum; and
    based on the measure of probability, outputting for display, during the conversation, a notice indicating that the first participant has exhibited a characteristic of autism.

2. The method of claim 1, wherein the training data comprises a second plurality of training examples, each example being a text of a conversation labeled as not exhibiting any characteristic of autism, wherein the ML model is generated using both the conversations labeled as exhibiting at least characteristic of autism and the conversations labeled as not exhibiting any characteristics of autism.

3. The method of claim 2, wherein generating the ML model comprises:
    identifying features in the conversations in the first and second pluralities of training examples using natural language processing, each of the features describing at least one of a pattern and a behavior in the conversations.

4. The method of claim 3, wherein generating the ML model comprises:
    assigning a respective weights to the features in the ML model.

5. The method of claim 1, wherein one of the features describes at least one of a pattern and a behavior in the textual conversation and corresponds to at least one characteristic of autism.

6. The method of claim 5, wherein evaluating the features with the ML model comprises:
    assigning weights to the plurality of features, wherein the weights represents a likelihood that a corresponding feature is a characteristic of autism.

7. The method of claim 6, wherein evaluating the measure of probability is based on a diagnosis score generated using the weights.

* * * * *